United States Patent [19]
Johnson

[11] Patent Number: 5,224,051
[45] Date of Patent: Jun. 29, 1993

[54] FLUID CONDITION MONITORING AND CONTROLLING SYSTEM FOR A METALWORKING FLUID CENTRAL SYSTEM

[75] Inventor: Jerry T. Johnson, Hamilton, Ohio
[73] Assignee: Cincinnati Milacron, Inc., Cincinnati, Ohio
[21] Appl. No.: 354,485
[22] Filed: May 19, 1989
[51] Int. Cl.$^5$ ................ G05B 19/417; G06F 15/46
[52] U.S. Cl. .................. 364/474.11; 364/474.19; 184/6.14; 340/825.06; 340/825.23; 72/42; 72/236
[58] Field of Search .............. 364/474.19, 474.06, 364/138, 148, 183, 500, 509, 510, 551.02, 474.15, 474.16, 474.11; 210/706, 739, 742, 743, 746; 184/6.0, 6.1, 6.14, 6.24, 7.4, 108; 29/DIG. 50, DIG. 54, DIG. 63; 252/49.5; 340/825.22, 825.23, 825.06; 137/1, 2, 4, 5, 92, 392; 408/56; 409/139; 83/169; 51/356

[56] References Cited

U.S. PATENT DOCUMENTS

| | | | |
|---|---|---|---|
| 3,618,707 | 11/1971 | Sluhan | 184/1 E |
| 3,638,191 | 1/1972 | Mann | 340/825.17 |
| 3,750,847 | 8/1973 | Sluhan | 184/1 E |
| 4,007,629 | 2/1977 | Hockstein | 73/53 |
| 4,053,743 | 10/1977 | Niemi | 364/500 |
| 4,105,092 | 8/1978 | Zeidler et al. | 184/6.4 |
| 4,115,956 | 9/1978 | Huffman | 51/96 |
| 4,269,604 | 5/1981 | Snowden, Jr. | 23/230 HC |
| 4,281,536 | 8/1981 | Kraft et al. | 73/53 |
| 4,315,421 | 2/1982 | Wilson | 137/92 |
| 4,527,661 | 7/1985 | Johnstone et al. | 184/6.1 |
| 4,573,115 | 2/1986 | Halgrimson | 364/138 |
| 4,629,334 | 12/1986 | Hockstein | 374/103 |
| 4,655,940 | 4/1987 | Harms | 210/805 |
| 4,757,878 | 7/1988 | Iino et al. | 184/6.4 |
| 4,767,982 | 3/1988 | Florig et al. | 324/632 |
| 4,779,451 | 10/1988 | Ezawa et al. | 73/53 |
| 4,825,207 | 4/1989 | Snell | 340/825.06 |
| 4,830,757 | 5/1989 | Lynch et al. | 210/742 |
| 4,852,693 | 8/1989 | Nakajima et al. | 184/6.14 |
| 4,931,187 | 6/1990 | Derham et al. | 210/742 |

OTHER PUBLICATIONS

"Report on Development of Automatic Monitoring Techniques for Water Based Cutting Fluids", Project RGF-71-4073-00, Production Engineering Research Association of Great Britain, C. Bowes & P.W. Wright, Apr. 1985.
Soviet Engineering Research, vol. 1, No. 4, 1981, Melton Mowbray GB pp. 89-90; N. Sereda et al.: "The Effect of the Concentration of Oxygen Dissolved in the Coolant on Cutting Tool Life".
Nalco Chemical Company, "Questions and Answers, Trendcheck Data Management Program", Mar. 1987.
Nalco Chemical Company, "Ram 64 Data Logging Controller", 1987.
Nalco Chemical Company, "Trendcheck Operators Manual", Version 2, 1987.
Nalco Chemical Company, "Potential Benefits of Nalco Ram 64 System", 1987.

*Primary Examiner*—Jerry Smith
*Assistant Examiner*—Paul Gordon
*Attorney, Agent, or Firm*—Wood, Herron & Evans

[57] ABSTRACT

A metalworking fluid central system through which aqueous cutting fluid recirculates through a plurality of machine tools is provided with an in-line fluid condition monitor which produces real-time fluid composition data for use in controlling the condition of the fluid. Four sensors simultaneously measure temperature, pH, dissolved oxygen and conductivity at hourly intervals and the data is stored in a computer module linked to the monitor. A plurality of diversely located plants are similarly equipped. A computer at a remotely located central monitoring facility selectively connects to the computer modules at the various plants through modems and a telephone system to collect the data daily. The data is analyzed at the central facility and dimensions are made manually and automatically to add components to the fluid at the respective plants or to take other corrective action. Commands and recommendations are communicated to the computer modules at the respective plants where they are manually and automatically implemented by the operation of valves, pumps or other devices or methods to modify the make-up of the fluid in the central system.

37 Claims, 6 Drawing Sheets

FLUID CONDITION MONITORING AND CONTROLLING SYSTEM FOR A METALWORKING FLUID CENTRAL SYSTEM

FIELD OF THE INVENTION

The present invention relates to central systems for recirculating metalworking fluid to a plurality of machine tools, and more particularly, to a method and apparatus for monitoring and controlling the condition of the cooling and lubricating fluid recirculated through such a central system.

BACKGROUND OF THE INVENTION

Machine tools conventionally employ metalworking or cutting fluid to lubricate and cool the cutting interface between the tool and the workpiece. These fluids serve the purpose of cooling and lubricating and in addition carry away the shavings and chips of material cut from the workpiece.

Metalworking facilities typically employ a number of cutting tools, many of which require similar metalworking fluids. Such facilities often employ what is referred to as the metalworking fluid central system. The central system collects and stores the metalworking fluid from a plurality of machine tools in a common reservoir and filters and recirculates the fluid between the reservoir and the tools.

In many metalworking applications, it is preferred to utilize water-based cutting fluids to take advantage of a higher heat absorption capacity than that provided by oils and non-soluble fluids. In addition, water-based fluids are preferred in many applications because they are less likely to contaminate the air and other aspects of the working environment within the facility. In addition, many water-based fluids are more economical, particularly when it is taken into account that they are biodegradable and may be more easily disposed of than petroleum based or other oil or organic based fluids. In addition, water-based fluids are generally not as flammable or explosive and thus less hazardous.

Water-based fluids, however, introduce other problems. Water-based fluids are more susceptible to loss by evaporation, provide a medium for the growth of biological contaminants, and, because of their biodegradability, are prone to attack by the microorganisms which can grow within them.

Water-based metalworking fluids generally fall into three categories. In one category includes soluble oils which are generally mineral oil. Another type of water-based metalworking fluid is the semi-synthetic fluid which is made up in part of mineral oil and in part by a combination of other synthetic lubricants. A third type of water-based metalworking fluid is the synthetic fluid which is made up entirely of synthetic components. The choice of cutting fluid is usually dictated by the particular machine operation and materials being worked.

With water-based metalworking fluids, a number of components are added to the water-based fluid solution in addition to the soluble oil or synthetic lubricant which provides the basic lubricating function. The additives include corrosion inhibitors which will coat the workpiece, the removed chips and the other metallic parts of the tools and other machine components which are subject to oxidation. In addition, emulsifiers are added to retain and disperse the oils throughout the solution so that they are available to provide lubrication at the point of cut. Corrosion protection is usually provided by the introduction of organic salts into the solution. Microbiocides are also an important component of water-based metalworking fluid systems. The water-based medium, in addition to the organic lubricant which provides food for microorganisms, requires biocidal ingredients to inhibit the growth of bacteria and mold. Other specific components are also required for various specific applications to maintain the appropriate fluid properties to cool and lubricate the particular cutting operation. The addition of buffers are added as well as caustic or other substances to control or alter the pH of the fluid.

Important in maintaining central systems is the desire that the properties of the cutting fluid be kept within controlled limits. The operating domain of the cutting fluids is generally a hostile environment in which many factors are at work which alter and degrade the cutting fluid. In addition to an overall degradation of the fluid, many specific cutting fluid properties and components are disproportionately affected when the environmental factors are allowed to act on the fluid. In addition to degradation of the fluid, loss of fluid occurs through evaporation, through the splashing out of fluids from the system, and from the carrying off of fluids on the parts and on the chips which are carried away. This may change the fluid volume and may also change the concentration of the various fluid components.

Evaporation, for example, will cause a loss of the water and also a loss of various fluid components in relation to their volatility. The carry-off phenomenon is more likely to deplete the lubricating oil component of a fluid which adheres to the parts and chips which are removed from the system. This is most often responsible for a loss in concentration of the corrosion inhibitors which, by their nature, adhere to the parts and the metal chips. Accordingly, make-up water must be added regularly. Oil or lubricant concentrates must be added to maintain their concentration in the fluid solution. Corrosion inhibitors must also be added to the fluid to compensate for their selective depletion.

The reservoirs of most central systems are usually located below floor level and thus are easily contaminated with bacteria and mold laden material. Such microorganisms breed in the solutions, attacking the emulsifiers, corrosion inhibitors and lubricant materials of the metalworking fluid. In addition, other lubricating and hydraulic oils and other foreign materials enter the metalworking fluid, some becoming emulsified within the fluid. These generally are a detriment to the fluid's performance and to the duration of its life.

Maintenance of a metalworking fluid central systems requires a controlling of the various properties and components of the metalworking fluid. Loss of cooling and lubricating capacity of the fluid can produce expensive and damaging results by increasing the production of scrap and by decreasing the life of tools and other machine components. A failure to control the properties of the fluid which prevent corrosion of the parts and cuttings results in increased waste due to the corrosion. In addition, increased contamination of the system with oxidation products reduces the lubricating effects of the fluid and the fluid's useful life.

Furthermore, a serious problem with water-based fluids results from failure to control microbiological growth in the metalworking fluid. Microorganisms in the fluid will, up to a point, grow with increasing rapidity if their growth is not checked in an early stage. The growth of these organisms tends to alter the system pH and otherwise change the environment in such a way as to facilitate increased growth rate of the micro-organisms. Since microorganisms feed on the lubricating components and other organic components of the fluid, they degenerate or degrade the fluid to the point where it loses its ability to lubricate, protect the parts, or to otherwise perform its function. This can prematurely end the life of the oil, accelerating the need for a complete replenishment of the fluid in the system. Fluid replacement may involve significant downtime, substantial cost for the replacement fluid, and additional expenditures in disposal of the spent fluids in accordance with environmental criteria.

The methods employed in the prior art to determine the conditions of the fluid in order to respond to changes in the fluid conditions have been inadequate to properly maintain the fluid. The common method of monitoring the properties of metalworking fluids has been to extract a sample of the fluid from the system, remove it to a laboratory, and perform a wet chemistry analysis upon the sample. Such procedures are generally regarded as capable of performing an accurate analysis on the properties of the fluid at the time, and under the conditions upon which, the test is made. However, the procedures are slow and, in many cases, changes in the sample result between the time the sample is taken and the time at which it is analyzed. This method of testing often produces data which are out of date due to the testing delay or inaccurate due to the change in the property being measured subsequent to the drawing of the sample.

Accordingly, corrective action taken is often too slow or at the wrong level to correct for the actual condition of the fluid at the time the correcting action is carried out. Thus, the corrections have been insufficient, resulting in considerable instability in the fluid property maintenance. As a consequence poor fluid performance results. Furthermore, the prior art systems have not resulted in the collection of data regarding the fluid's properties in a combination sufficient to make it possible to detect and determine the causes of fluid problems and to indicate the appropriate corrective response.

SUMMARY OF THE INVENTION

It has been a primary objective of the present invention to provide a method and apparatus for monitoring and controlling a metalworking fluid in a metalworking fluid central system servicing a plurality of machine tools. It has been a further objective of the present invention to provide a quick and accurate system for measurement of metalworking fluid parameters in real time so as to facilitate accurate and responsive correction of deviations from ideal fluid conditions so that the fluid performance may be effectively and satisfactorily maintained.

It is a more particular objective of the present invention to provide a method and apparatus by which metalworking fluid monitoring data can be quickly and accurately collected from a plurality of metalworking fluid central systems and analyzed at a remote location from which determinations can be made for corrective control of the fluid to be performed on a real time basis. It is an additional objective of the present invention to provide such a method and apparatus in which the monitored data may be processed and decision making commands initiated to automatically control the chemical composition and physical characteristics of a metalworking fluid to maintain the fluid within certain controlled parameters.

According to principles of the present invention, a metalworking fluid central system is provided with inline monitors for measuring fluid properties by the provision of a plurality of inline sensors responsive to a plurality of different fluid properties. The sensors generate real time output signals responsive to levels, changes or trends in the sensed parameter values. The parameters sensed include among those sensed parameters relating to specific chemical components of the fluid, preferably, dissolved oxygen gas concentration and hydrogen ion concentration (pH). In accordance with the preferred embodiment of the invention, other parameters sensed include electrical conductivity and temperature. This data is digitized and stored in a storage medium through a computer located at the central system. In accordance with a further preferred embodiment of the present invention, the central system is also provided with a plurality of additive sources connected through pumps, valves or other fluid control devices to inject make-up water, lubricant concentrate, buffers, microbiocides and other such additives in order to provide for various actions which would be indicated by the measurements to correct the properties of the fluid. Such devices are linked through a controller having inputs driven directly by the computer, and by controls manually operated in response to messages displayed as a result of the processing of the measured data by the computer.

Further in accordance with a preferred embodiment of the present invention, the computer is linked through a conventional modem to a telephone switching network. This central system and other central systems which are also provided with monitoring and controlling features of the invention and similarly linked through the telephone switching network, are selectively connectable to computerized equipment at a remote central office supervising facility. The computer at the central station or center is programmed so as to periodically establish a communications link through the telephone exchange with each of the various machining facilities to extract data collected and stored in the central system computer for transfer to and analysis at the central location. Preferably, the interrogation to collect data for analysis occurs at programmed intervals of, for example, 24 hours, with more frequent checks made for unusual or alarm conditions. This data may be used in whole or in part either through the computer at the central system or from the central processing center to establish automated commands to signal or directly control the introduction of various additives to correct parameters of the fluid. Preferably, the data is analyzed and decisions made at least in part with operator or manual intervention at the central or machine location to either take corrective action or override automated corrective commands. The information may preferably include data from a plurality measurements taken at spaced timed intervals, preferably hourly, which may be analyzed at the central monitoring center and trends of the fluid in the respective central systems determined for establishing and supervising a maintenance program, to schedule maintenance visits and to dispatch supplies of chemical components to the various facilities.

The advantages of the present invention are that data can be gathered which is accurately derived from inline samples, is representative of the real time condition of the fluid and is available for real time decision making and response in time make the corrections necessary to effectively maintain control of the fluid. As a result, the life of the fluid is lengthened, the ability to quickly and rapidly respond to fluid changes is provided, and significant and accelerating degeneration of the fluid is prevented, along with the resulting loss in fluid performance, increase in waste, and increase in cost of the operation.

These and other objectives and advantages of the present invention will be more readily apparent from the following detailed description of the drawings in which:

BRIEF DESCRIPTION OF THE DRAWINGS

FIGS. 3-6 are graphs of the operation of one metalworking fluid central system operating under controlled conditions and respectively plotting temperature, conductivity, pH and dissolved oxygen as a function of time;

FIGS. 7 and 8 are graphs similar to FIGS. 3-6 of the operation of another metalworking fluid central system which is biologically out of control and respectively plotting conductivity and dissolved oxygen as a function of time; and FIGS. 9 and 10 are graphs similar to FIGS. 3-8 of the operation of another metalworking fluid central system experiencing a fluid containment failure and respectively plotting dissolved oxygen and pH as a function of time.

Referring to FIG. 1, a metalworking fluid monitoring and control system 10 according to the principles of the present invention is illustrated. In the preferred and illustrated embodiment there represented, the monitoring and control system 10 is a multifacility monitoring and control system distributed among a plurality of diverse locations which include a central information monitoring data analysis and supervisory location 11, a plurality of differently located metalworking plants 12, 12a, and 12b, and a communication system 13 through which are established communications links between the central location 11 and each of the plants 12, 12a, 12b. Preferably, the communications link 13 is a public telephone communications system which includes one or more telephone switching networks 14 of the various public or private telephone systems for routing telecommunications information between the telephone line 15 between the central location 11 and the telephone exchange 14 and the telephone lines 16, 16a and 16b which connect the telephone exchange 14 with the respective plants 12, 12a, 12b. It should be readily appreciated that, while telephone lines 15, 16, 16a and 16b are described as wires, other transmission media may make up the communications links, and that alternatives to the preferred telephone communications approach may be employed.

Figure 1:
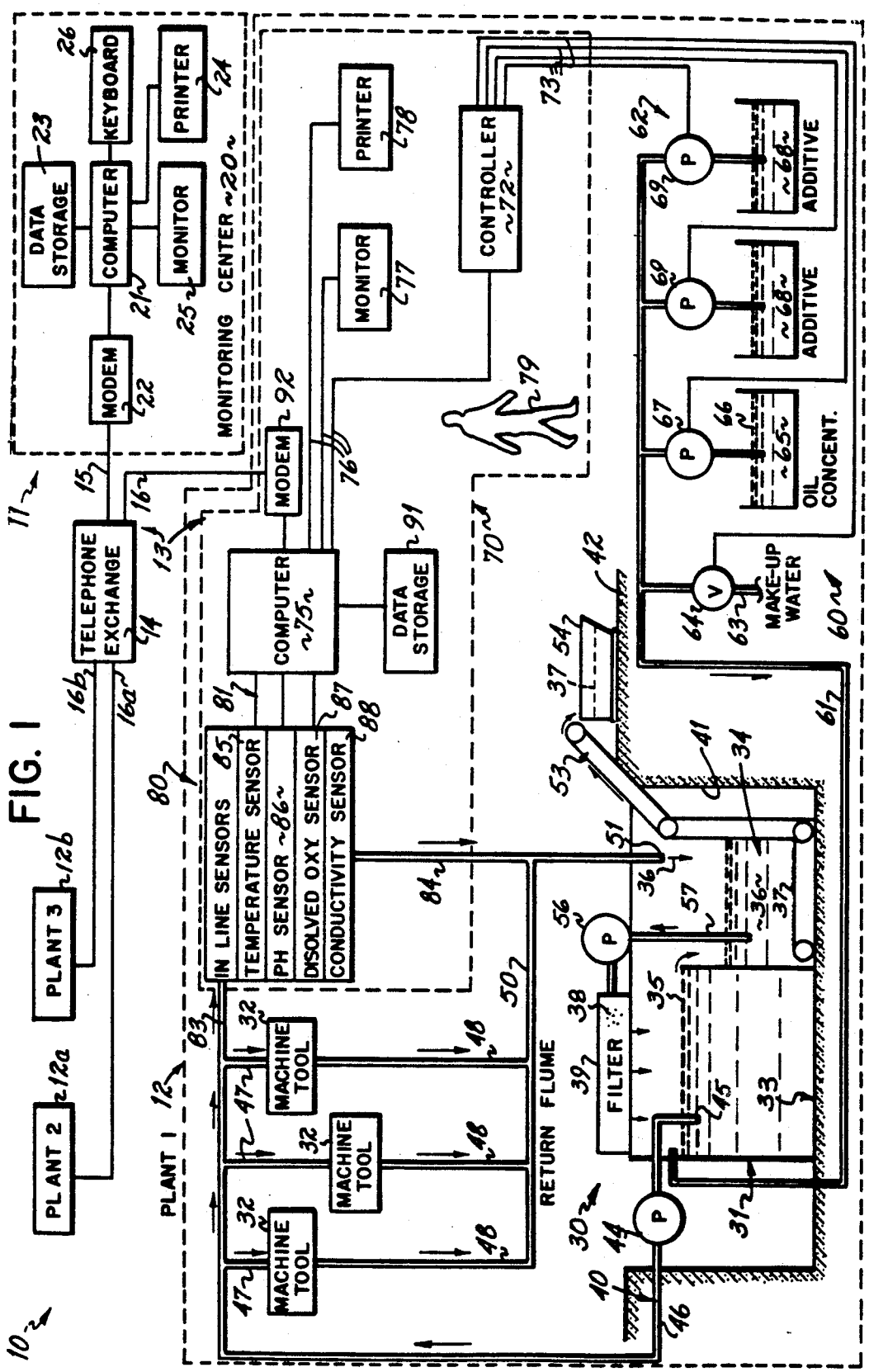
FIG. 1 is a block diagram of a metalworking fluid central system which includes the fluid monitoring and control system in accordance with principles of the present invention.

At the central location 11 is a metalworking fluid monitoring center 20 which includes a computer 21 connected through a modem 22 to the telephone line 15. The computer 21 has connected thereto a data storage medium 23, which is preferably a disk or other non-volatile data storage medium, a printer 24 which is capable of generating hard copies of visually perceivable data, data records or files, a monitor 25 which is capable of online and random access display of the information which passes through or is stored in the computer 21, and a keyboard or other computer/supervisor interface device 26.

The system 10 components present at each of the plants 12, 12a, 12b are diagrammatically illustrated for plant 12 in FIG. 1. The plant 12 is a metalworking facility which is equipped with a metalworking fluid central system 30. The system 30 operates to recirculate a cutting or metalworking fluid through a fluid reservoir 31 to and through a plurality of machine tools 32. The reservoir 31 is divided into two parts, a clean fluid tank 33 and a dirty fluid tank 34. The clean fluid tank 33 contains a level of metalworking fluid 35 in its clean and controlled condition as supplied to the machine tools 32. The dirty fluid tank 34 receives the used fluid 36 which is returned from the machine tools 32 after use. The dirty fluid 36 is the portion of the clean fluid 35 which also includes solid metal chips and other particulates 37 which precipitate to the bottom of the tank 34 and fine suspended particulates 38 which are separated from the fluid 35 in a filter 39.

The central system 30 includes a fluid recirculating network 40 for recirculating the fluid 35 through the reservoir 31, through the machine tools 32 and back to the reservoir 31. The reservoir 31 is typically positioned within the pit 41 below the floor level 42 of the plant 12. The machine tools 32 are generally mounted on the floor 42 to stand thereabove. The recirculating system 40 includes a fluid pump 44 located within the pit 41 adjacent the reservoir 31 and having inlet 45 connected with the clean fluid tank 33 in such a way as to draw clean fluid 35 from the tank 33. The pump 44 has its outlet connected to a supply line 46 which communicates through the floor 42 of the plant 12 to the inputs 47 of the machine tools 32 for deliverying clean cutting fluid 35 to the machine tools 32. At the machine tools 32, the fluid 35 is, in a manner conventional to and specific to these individual machine tools 32, provides a cooling and lubricating function at the point of cut between the cutting tool component and the workpiece. The fluid also carries from the cutting site dirty fluid 36 which is made up of the clean fluid 35, and chips 37 and other cut and foreign material from the workpieces to remove it from the cutting site. The fluid 36 returns through metalworking fluid drain lines 48 from the machine tools 32 and then a return flume 50 within the floor 42 of the plant 12 to the dirty fluid tank 34.

A return flume 50 is often an open drain built within the floor 42 of the plant 12. Into the flume 50 drains not only the dirty fluid 36 from the lines 48, but also other foreign liquid and solid materials including solvents, spilt lubricants, and other contaminants. These contaminants flow with the fluid by gravity through the flume 50 which slopes downwardly into the pit 41 to a discharge opening 51 which empties the dirty fluids 36 into the return tank 34. In the tank 34, the chips and other cuttings 37 generally descend to the bottom. From the bottom of the tank 34, the chips 37 are removed from the return tank 34 by a drag out conveyor mechanism 53 which removes the chips 37 from the tank 34, transports them upwardly from the pit 41 to above the floor 42, and deposits them into a hopper 54 for recycling.

From the tank 34, the dirty fluid 36, less the removed chips 37, is pumped through a pump 56 into the filter 39 which removes other smaller dust and other solid particulates which have not precipitated to the bottom of tank 34 from the fluid to deliver cleaned fluid 35 to the clean fluid tank 33. Line 57 is the inlet line from the tank 34 for the pump 56.

A fluid makeup system 60 is also provided to restore or add components to the fluid 35 within the reservoir 31. The makeup system 60 includes a supply line 61 which connects a plurality of component sources 62 with the tank 33. The sources 62 generally include a make up water supply line 63 which is connected from a pressurized source of clean supply water through a control valve 64 to the line 61. In addition, the makeup sources 62 of the makeup system 60 include a supply tank 65 of clean metalworking fluid concentrate through which the concentrate 66 is pumped through a pump 67 to the makeup fluid supply line 61 and into the clean fluid tank 33. In addition, a plurality of additive sources 68 are provided to supply different additives to the fluid 35. These additives are communicated through delivery systems which may include pumps or valves 69.

The monitoring and control system 10 includes a cutting fluid monitoring and control network 70 at the located plant location 12. The control network 70 includes a controller 72 for operating the equipment which delivers the additives from the make up system 60 to the fluid 35 in the reservoir 31. The controller 72 has a plurality of outputs 73 each of which connect to a different one of the control devices 64, 67 and 69 which regulate the addition of make-up water from the source 63, make-up concentrate from the source 65, and other fluid additives from the sources 68.

The network 70 also includes a computer 75, preferably an industrial grade programmable computer, having outputs 76, one of which connects through an output to the controller 72 for communicating command signals from the computer 75 to the controller 72. The computer 75 also has outputs 76 which connect to a monitor 77 and to a printer 78 for displaying, in visually perceivable form, information from the computer 75 for use by an operator 79 in entering control commands into the controller 72.

The monitor and control network 70 also includes a sensor module 80 which generates electrical output signals on a control line 81 connected to an input of the computer 75. The sensor module 80 contains a plurality of sensing devices for measuring characteristics of fluid 35 flowing therethrough. The module 80 is connected in-line with the fluid recirculating system 40 so as to measure characteristics of clean recirculating fluid 35. The module 80 has an inlet 83 connectable to the supply line 46 and an outlet 84 connectable to the return flume 50. As such, a fluid bypass is formed from the supply line 46 past the machine tools 32 and to the return tank 34 of the reservoir 31.

The sensor module 80 includes a temperature sensor 85, a pH sensor 86, a dissolved oxygen sensor 87 and a conductivity sensor 88. The sensors 85, 86, 87 and 88 measure respectively the temperature, pH, dissolved oxygen content and conductivity of the fluid 35 as it flows in line through the sensor module 80 and does so in real time. The outputs of the sensors 85-88 are communicated through the output line 81 to the computer 75. From the computer 75, the data from the sensor module 80 is stored in a data storage medium 91 at the network 70. In addition, the computer 75 connects through a modem 92 to the telephone line 16 so that the computer 75 will communicate through the telephone exchange 14 of the communications network 13 with the computer 21 at the central location 11.

Figure 2:
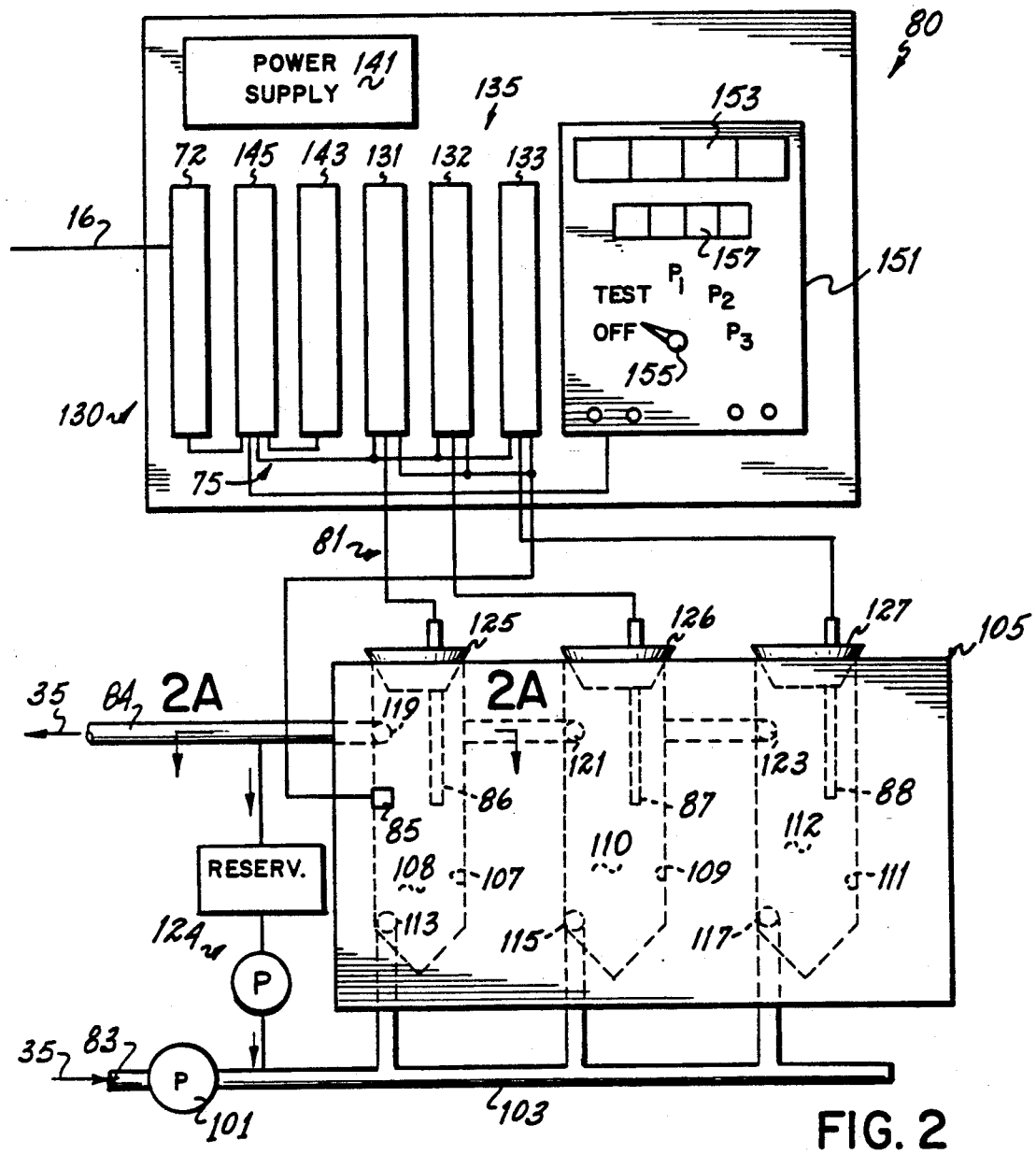
FIG. 2 is a schematic diagram of the central system sensor module of the system of FIG. 1.
Figure 2A:
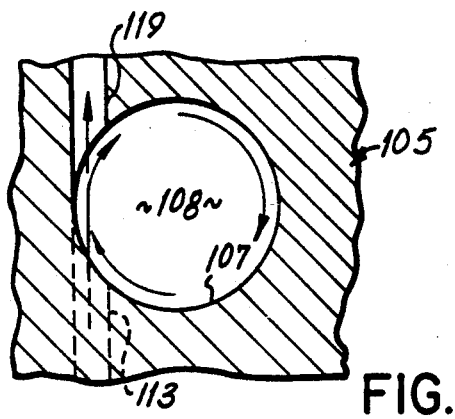
FIG. 2A is a diagrammatic cross-sectional view taken on lines 2A—2A showing the fluid flow pattern within the sampling chamber of the monitor of FIG. 2.

Referring to FIG. 2, the sensor module 80 is described in greater detail. The module 80 is a type of water monitor module manufactured by Schneider Instrument Company, 8115 Camargo, Road, Madeira, Ohio. The module 80 is shown having its inlet 83 connected to receive clean, or more precisely, clarified metalworking fluid 35 from the supply line 46 and to discharge the fluid 35 through the outlet line 84 to the return flume 50. The fluid 35 flowing through the module 80 is maintained at the proper pressure and flow rate by an inlet valve 101 connected in the line 83. From the valve 101 is a bank of feed pipes 103 which communicate the clarified fluid 35 to a sampling block 105 which contains the sensors 85, 86, 87 and 88. In the embodiment shown, the block 105 includes three bores 107, 109 and 111 each having at the bottom thereof an inlet 113, 115 and 117 respectively connected from the pipe manifold 103. The bores 107, 109 and 111 form sampling chambers 108, 110 and 112 therein. The inlets 113, 115 and 117 are positioned with respect to the chambers 108, 110 and 112 such that fluid entering the chambers does so with a swirling action to fill the chambers and to mix with the fluid therein to prevent separation of its components. At the tops of the chambers 108, 110 and 112 are respectively located outlet ports 119, 121 and 123 each connected to the outlet line 84. By this port arrangement, the fluid enters and swirls through the chambers to the outlets as shown with respect to chamber 108 in FIG. 2A. As such, the fluid in the chambers remains fresh and oil and other material which might have a tendency to float to the top of the fluid and collect in spots within the chambers 108, 110 and 112 will not have the opportunity to do so.

The cutting fluid 35 is continuously recirculated through the chambers 108, 110 and 112 of the block 105 during sampling intervals. At various times between the sampling intervals, clean fresh water is circulated through the chambers 108, 110 and 112 in order to maintain the internal surfaces including sensors therein clean and extend their lives. This is provided by a water inlet and valve combination 124 connected as a by-pass line from the outlet line 84 to the inlet line 83 to operate alternately with the valve 101.

The pH sensor 86 is supported through a sealing cap 125 at the top of the chamber 108 to support the pH sensor 86 in spaced relationship from the walls of the chamber 108 and in the in-line stream of fluid 35 flowing through the chamber 108. Also in the chamber 108 is the temperature sensor 85. A sensor 85 may be provided in each chamber. In similar manner as with the sensor 86, the dissolved oxygen sensor 87 is supported through a cap 126 in the chamber 110 and the conductivity sensor 88 is supported through a cap 127 within the chamber 112.

The sensors 85, 86, 87 and 88 connect through output cable 81 to the inputs of a processing or computer module 130 which includes the computer 75 and the storage medium 91. The output from the sensors 86, 87 and 88 each go to a respective analyzer board 131, 132 and 133 respectively of a bank of analyzer boards 135 which may include inputs from other sensors. The output of the temperature sensor 85 is connected to the processor so as to interact with each of the boards 135. The reason for the connection of the temperature sensor to each of the boards is that the other three sensors measure properties of the fluid 35 to determine characteristics of the fluid 35 while the temperature sensor primarily collects information for temperature compensation of the other measurements. Accordingly, the information from the temperature sensor is required by the analysis performed by each of the boards 131, 132 or 133.

The analyzer boards 135 operate to separate the measured signal from noise, to adjust the analog signals from the sensors and to convert the signals to corresponding digital signals.

Also within the module 130 is a power supply 141 which operates the components within the module 130 and delivers energy for the operation of the sensors 85, 86, 87 and 88. The module 130 also contains a memory board 143 which is connectable to each of the processing boards 135. The memory board 143 which contains a non-volatile EARAM for storing the processing program and which contains the data storage medium 91. The computer module 75 also includes a general processing board or CPU 145 which executes the program stored in the board 143. Together the boards 143 and 145 function to sample the probes 85, 86, 87, 88 at periodic intervals and to produce digital data corresponding to the regular sampling intervals regarding the measured characteristics of the fluid 35. Additionally, a communications board is provided which is generally an RS232C serial output board and modem 72. The communications board or modem 72 is connected to the telephone line 16 (as shown in FIG. 1).

The controller board or computer 75 has the panel 151 having a first display 153 which operates in conjunction with a selector switch 155 so that the readings from each of the probes 85, 86, 87 and 88 may be independently displayed on the panel 153. The panel 153 is generally located above the controller 72 of FIG. 1. The panel 151 also contains a 24 hour real time clock 157. The components of the panel 151 are connected to the computer module CPU board 145.

Referring again to FIG. 1, the operation of the monitoring and controlling system 10 is better understood. The monitor control network 70 at the plant 12 will operate under control of the computer 75 to perform regular sampling measurements of temperature, pH, dissolved oxygen content and conductivity of the fluid 35 inline and in real time as it circulates through the recirculating system 40 of the central system 30. These measurements are processed through the equipment which was been described in connection with FIG. 2 above and stored, preferably at hourly intervals in the data storage medium 91. This data may be tested in real time in accordance with algorithms stored in the program module of the computer 75 to test for alarm conditions. Upon the occurrence of an alarm condition, a signal is generated to alert the operator 79 through the monitor 77, printer 78, or control panel 151 (FIG. 2) to take corrective action. In addition, the alarm conditions, should they be detected, according to certain embodiments of the invention, cause the computer 75 to activate the modem 92 to connect the system 70 on line with the telephone line 16 to communicate the data through the telephone exchange 14 of the communications network 13 to the monitoring center 20 at the central location 11.

In the normal course of operation, the monitoring center 20 at location 11 will periodically establish a telephone communication or other communication link through the network 13 to the plant 12 so that the computer 21 will communicate via the modem 22 and modem 92 with the computer 75. This communication will cause a transfer of the data stored in data storage medium 91 from the plant 12 to the central location 11. This communication established from the central location 11 will occur, typically, once per 24 hour period and will involve a transmission of records of data from the data storage medium 91, each time marked, to the computer 21 at the location 11. At the location 11, this information is processed in accordance with standard statistical process control techniques with software at the computer 21 and thereupon analyzed.

The interrogation by the monitoring center 20 of the plant 12, may occur typically once per day, but should take place at least at such intervals as will effectively result in analysis of the data in real time so that real time responses may be made to changes or trends which are revealed by the analysis of the data. By "real time" it is meant that an analysis is performed in sufficiently short proximity in time to when the test or data sampling has been made by the sensors of the sampling module 80 so that corrective action will be possible while the data is still valid and while the condition measured still exists both in a qualitative and quantitative sense. Such interrogation may be continuous or instantaneous if required or may be spaced at such intervals which are sufficiently short to provide real time analysis and real time response within the meaning of the terms as defined above.

The measured values of data will all be transmitted to the central monitoring center 20 at the central location 11. Of these values, it has been determined, in the preferred and illustrated embodiment, that temperature, conductivity, pH and dissolved oxygen should be measured simultaneously to provide related data groups for purposes of the analysis. It will be appreciated that measurement of other parameters may also be desirable, such as measurement of the concentrations of specific components of the fluid 35.

The temperature measurement is important in that the temperature of the metalworking fluids 35 in a central system 30 may vary considerably during use. The changes in temperature of the fluid 35 occur with the changes in atmospheric temperature and with variations of the fluid temperature due to the use of the equipment. The temperature itself provides information regarding the events at the plant site 12 which may have a bearing on the condition of the fluid 35 and may be helpful in the interpretation of other data or in diagnosing causes of changes in fluid condition. In addition, and perhaps more importantly, the temperature of the fluid is important for performing temperature compensation upon other data and for interpreting the other measurements made of the fluid. Certain of these measurements are automatically temperature compensated at the sensing module 80 and within the computer module 75 at the plant location 12. In addition, the measurement of temperature of the fluid 35 may itself be important particularly to high tolerance machine operations where dimensional changes caused by temperature may effect the quality of the parts produced. The temperature signal is derived in the first instance from the sensor 85.

The conductivity measurement is obtained from the conductivity sensor 88. The conductivity bears with the composition of the fluid 35. Measured conductivity will change as the concentration of the metalworking fluid in the water changes. In addition, dissolved solids in the fluids will also cause changes in the conductivity. Conductivity will provide a relative indication of concentrations of particular components. The identity of the particular components which are affecting conductivity changes depends on the amount of knowledge of a person or program interpreting the data as with respect to the component in the solution which is most rapidly changing. Accordingly, the present invention provides for the simultaneous real-time measurement of plural parameters of the fluid to facilitate identity of the causes of such data trends. Conductivity as a means for measuring concentration of a particular component of the fluid thus is most advantageously performed when interpreted in conjunction with such other data. It has been found that measuring of conductivity in conjunction with measurements of pH and dissolved oxygen, for example, provide considerable information as to the composition and composition changes in the fluid. With the conductivity measurement, relative changes in the measurement including particularly trends established by the changes and the rates of changes over time provide significant information of the nature of events occurring at the central system 30 which is being monitored.

The pH of the fluid 35 measured by the sensor 86 is a widely used electrochemical parameter employed in the management of metalworking fluid systems. It is found, however, that obtaining an accurate pH measurement is sometimes difficult. Measurement of pH is important in that maintaining a desirable pH at a level of, for example, 9.1, will reduce the growth of bacteria and other microorganisms within the fluid. pH may change from a number of sources such as with the introduction of substances into the fluid during the normal course of maintaining the central system 30. For example, the flushing of the return flume with solvents often affects the pH. Chemical action within the fluid may do the same. The introduction of contaminants during the normal course of operating the system may also effect the pH. It is necessary to add substances to the fluid from time-to-time in order to maintain the pH at a desirable level in order that the growth of microorganisms does not escalate.

The growth of microorganisms in a system, even a system with maintained pH, will nonetheless occur. When the system pH drops to, for example, a level of 8.5 or 8.6, the conditions for the growth of microorganisms, particularly bacteria, greatly increase. The growth of bacteria causes the expulsion of a substance which further tends to neutralize or lower the pH of the fluid. This may then cause the fluid to become even a more favorable environment for the growth of bacteria. This can in turn cause a rapid increase and escalation in the growth of bacteria such that, if not responded to quickly enough, can cause a total destruction or bacterial consumption and breakdown of the fluid.

The growth of micro-organisms such as bacteria will, in the first instance, cause a consumption of the oxygen dissolved in the fluid. Because of the high degree of agitation in the fluid and its exposure to ambient air, the dissolved oxygen in the fluid is usually near saturation, often even above the saturation point. Thus, the growth of bacteria can easily occur and substantial amounts of oxygen present in the fluid will support the bacterial growth. As bacteria grow, the oxygen level of the fluid will decline. A decrease in the dissolved oxygen content of the cutting fluid is often a very good indication of the ongoing growth of bacteria or molds.

Measurement of dissolved oxygen in order to establish ongoing trends by grab sampling of the fluid, as is done in the prior art, has proved an inaccurate method for deriving information in order to reliably detect microorganism growth. The inline measurement methods of the present invention, however, provide precise evenly spaced measurements of fluid oxygen content which may be developed at the monitoring center 20 into accurate trend data. This trend data will reveal microorganism activity. Accordingly, comparison of this data with pH data taken simultaneously with the dissolved oxygen measurements will allow for the determining of the causes of change in pH and for predicting possible destructive changes in the fluid composition which would result unless certain corrections are made. Furthermore, correlation of this data with the conductivity data regarding the composition of the fluid provides different sources of data which react differently to organic, biological, and ionic fluid components. These when analyzed from simultaneous measurements in accordance with the trends of each, provides for the detecting of fluid conditions which have not been previously realizable until employed in accordance with the present invention in combination.

The system of FIG. 1 operates to perform the same monitoring functions on a plurality of different plant locations 12, 12a, 12b, etc., so that analysis and corrective action may be taken for a number of facilities and also so that the supervising of a maintenance program from the monitoring center 20 may be optimized in such a way as to efficiently supervise a number of central systems 30 at different plants 12.

FIGS. 3-10 show comparative data analyzed in accordance with the present invention for three different plants during separate time periods each spanning approximately 6 days. The first data sampling group is illustrated in connection with FIGS. 3-6. FIGS. 3-6 show typical data from a 27,000 gallon centerless grinder operation using semi-synthetic fluid in a high production precision parts manufacturing process. On the graphs 3-10, the large marks are representative of days, each signifying midnight of the given day. The small marks represent hourly intervals at which the readings are taken as to provide a relatively continuous curve approximated by the curve in the figures.

Figure 3:
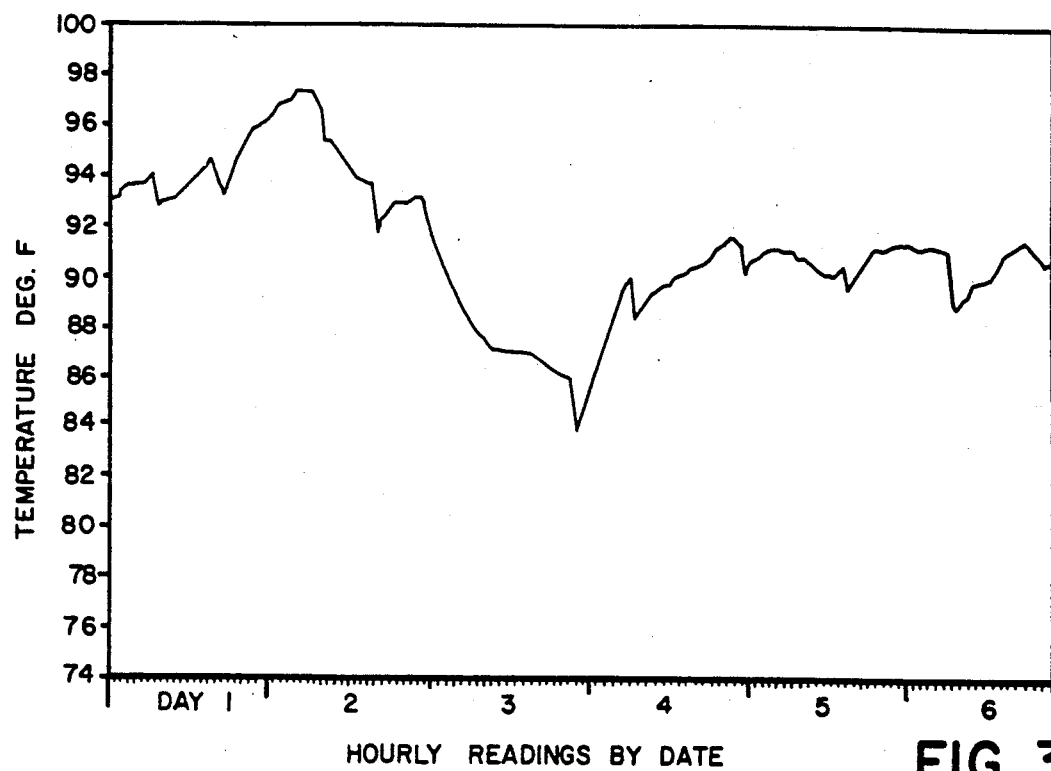
FIGS. 3-10 are graphs generated by the system of FIG. 1 illustrating data analyzed in accordance with the present invention.

As FIG. 3 illustrates, a temperature profile over the period of approximately 6 days is illustrated. The graph illustrates a significant temperature variation over the period along with periodic small reductions in temperature. The slow wide fluctuations in temperature were, in this case, due to ambient temperature changes with the low point occurring when production slowed during a weekend period. The small period temperature reductions were caused, in this case, by regular batch additions of makeup fluid injected, for example, from a supply 63 of makeup water together with the addition of concentrate 66 from the concentrate source reservoir 65. These makeup sources were maintained at lower temperature than the fluid 35 recirculating in the central system 30 at the time they were added.

Figure 4:
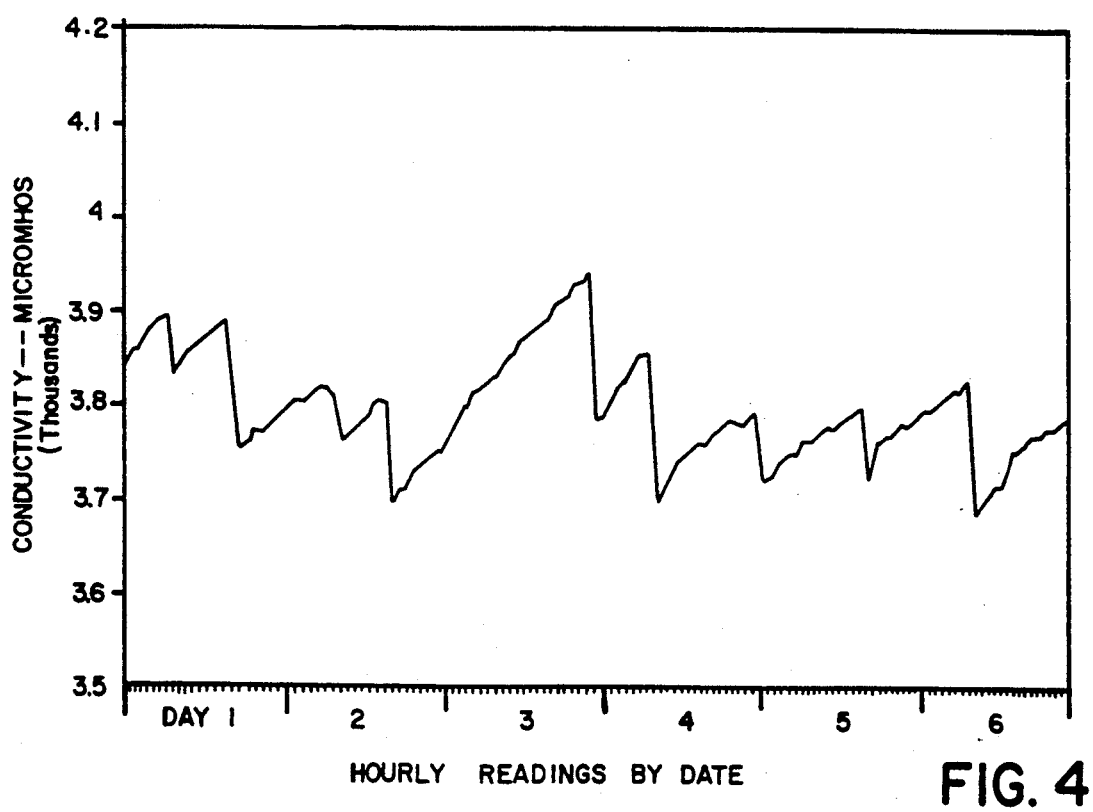

In FIG. 4, the conductivity of the same fluid plotted in FIG. 3 over the same time period is illustrated. The conductivity measurement is characterized by a plot of sawtooth profile as shown in FIG. 4. The portions of the curve which steadily increase demonstrate fluid concentration increases seen as a conductivity rise of the fluid due to evaporation of water from the system. Thus, the concentration of all components of the fluid are increasing during these periods at which the slope of the line shows conductivity increase. The sudden step drops in conductivity correspond to the addition of make up fluid as was described in connection with FIG. 3. The combined data in FIGS. 3 and 4 confirm that the addition of makeup fluid is responsible for the short term variations in the measured temperature and conductivity of the fluid. Additionally, the vertical displacement of the declining steps in FIG. 4 are an indication of the quantity of makeup fluid being added.

Figure 5:
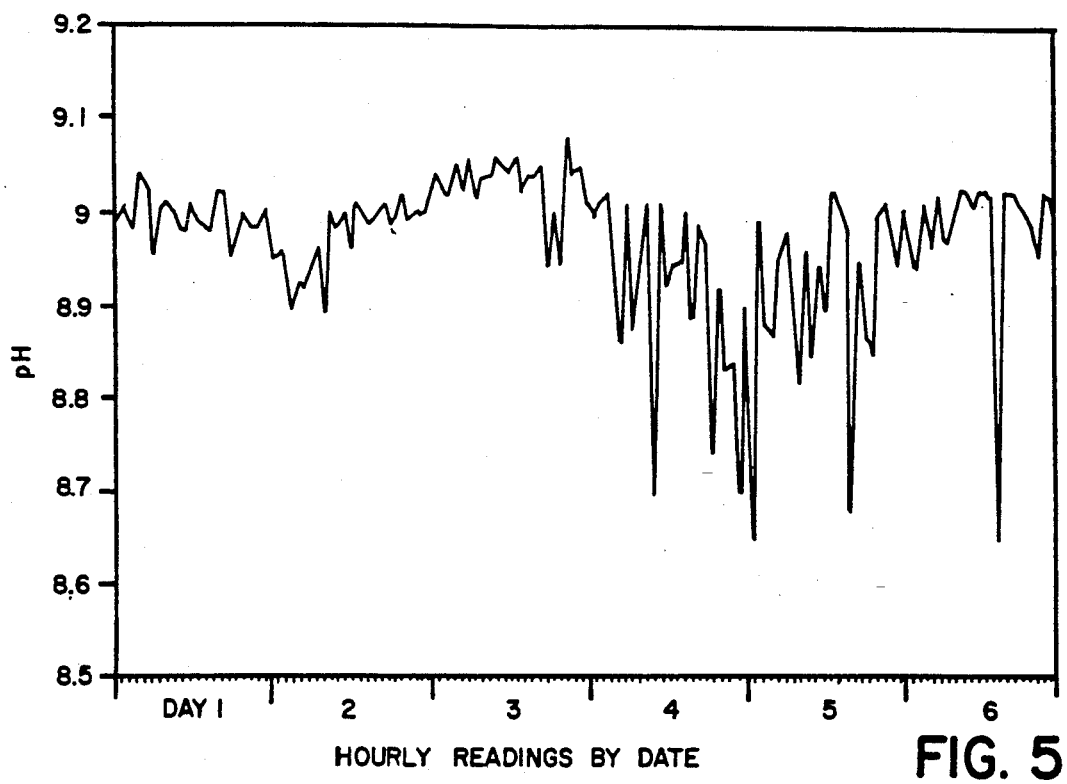
Figure 6:
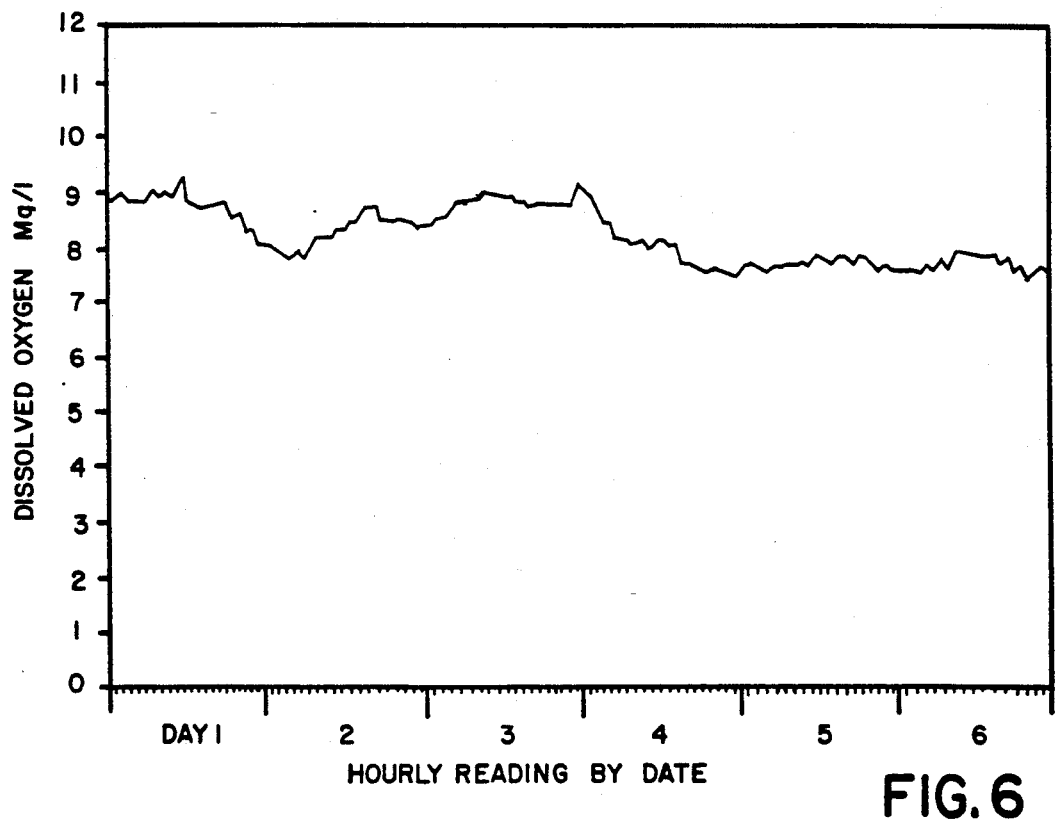

Referring to FIGS. 5 and 6, the measurements of pH and dissolved oxygen for the same fluid plotted in FIGS. 3 and 4 are shown during the same interval of time. The relative smoothness of the graphs, particularly of the dissolved oxygen plot of FIG. 6, shows that the system is relatively free of biological activity. The more rapid fluctuation of the pH curve of FIG. 5 shows however that concentrations of nonbiological components are changing. For the first half of the graph, these fluctuations are within tolerable limits. The more severe spikes toward the second portion of the graph are indicative of the addition of specific additives to the system during that portion of the time period. Generally, the condition of the fluid depicted in FIGS. 3-6 shows a relatively well behaved fluid and one which is within control limits.

Figure 7:
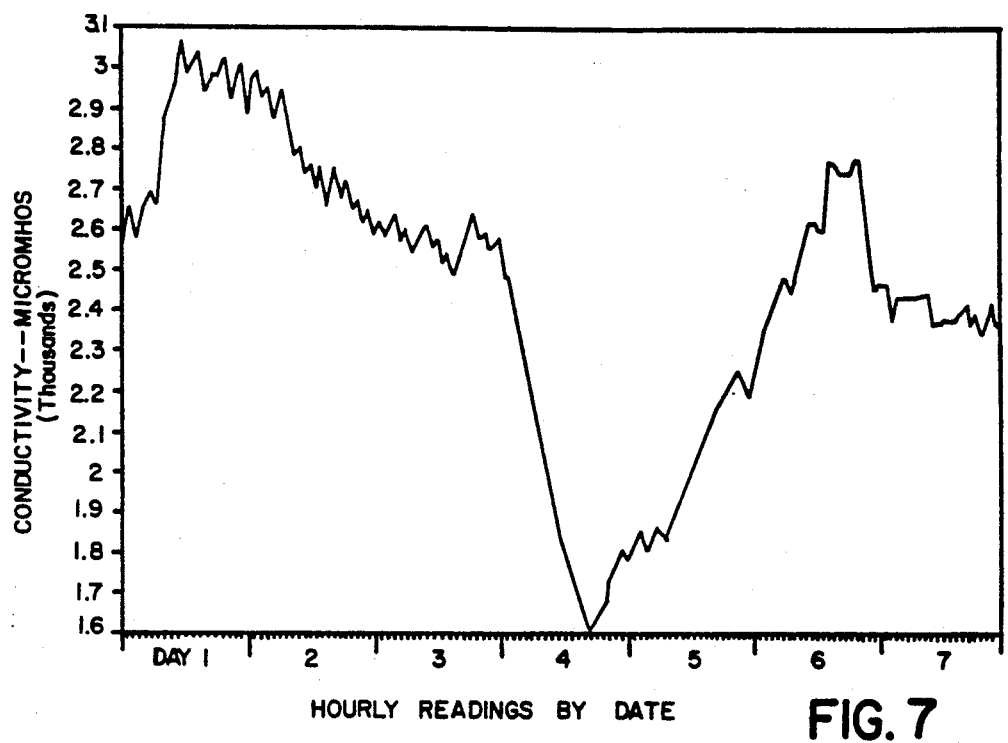
Figure 8:
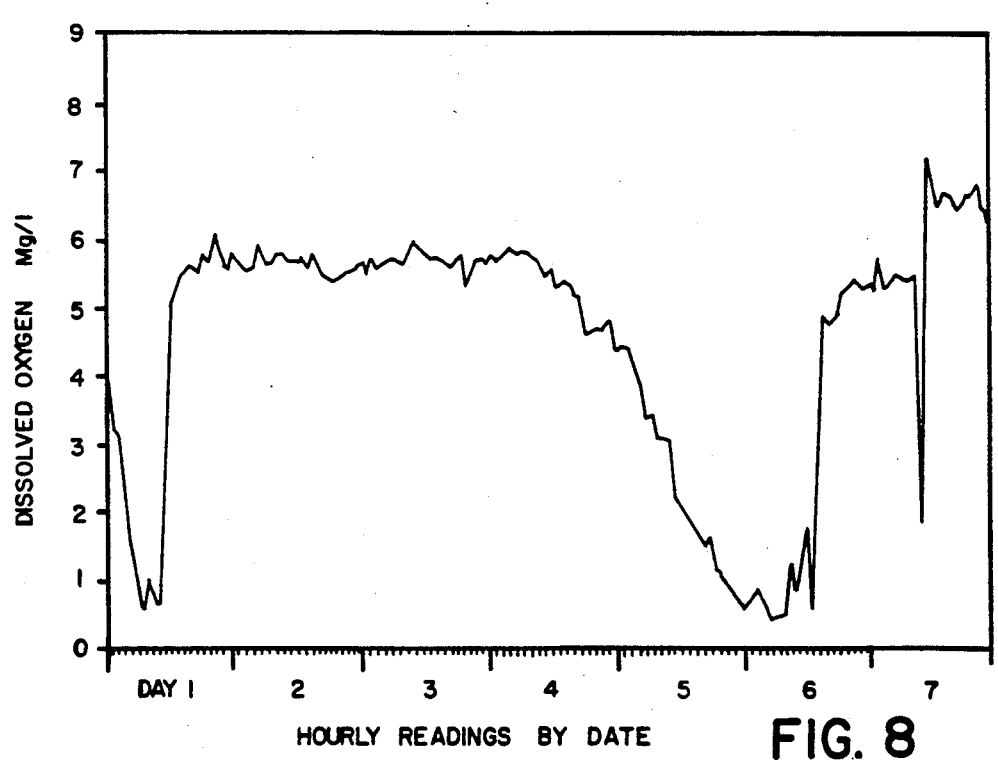
Figure 9:
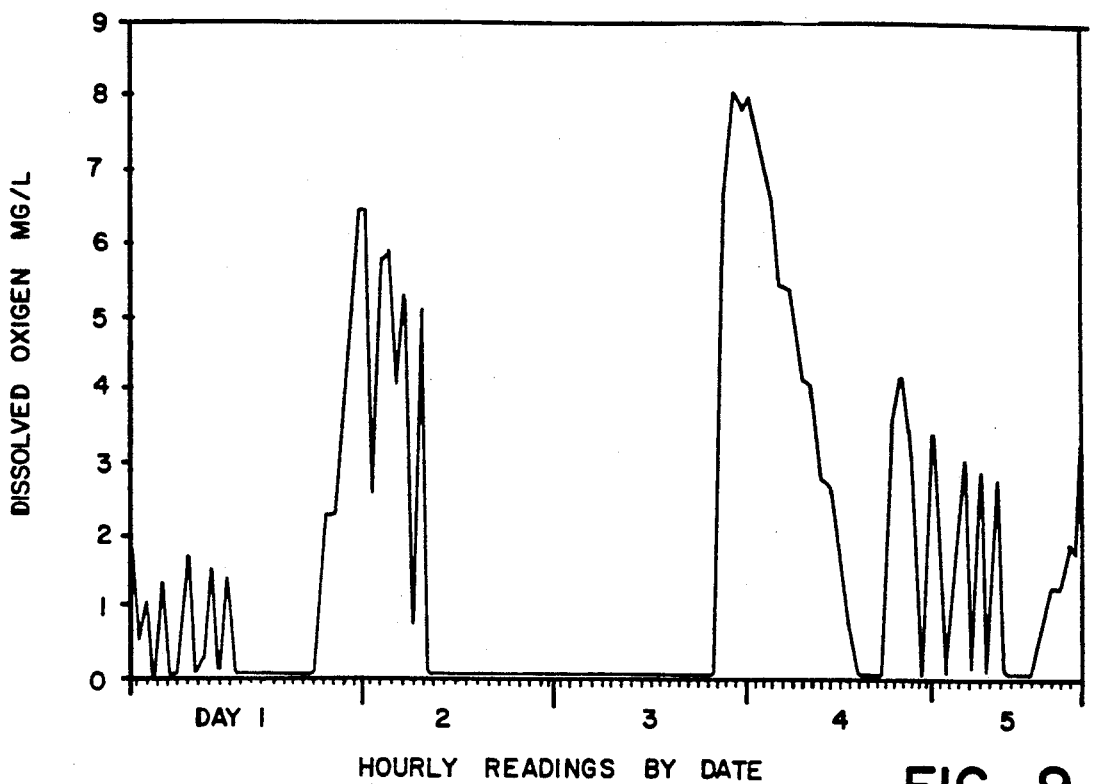
Figure 10:
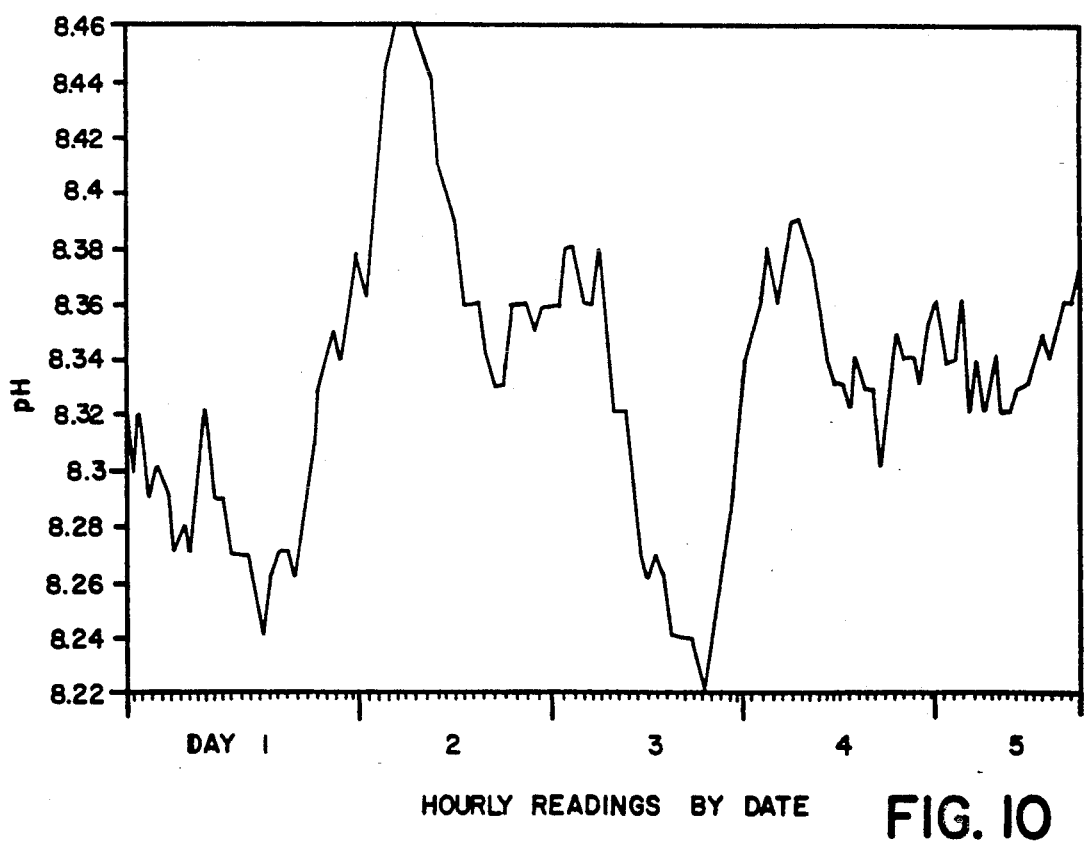

The combination of graphs of FIGS. 7 and 8 and the combination of FIGS. 9 and 10 show abnormal conditions of fluid in two different systems. The conditions shown in FIGS. 7 and 8 are examples of a mechanical failure of a central system 30 which shows up on the data monitored at the monitoring center 20.

Referring to FIGS. 7 and 8, the conductivity and dissolved oxygen respectively are illustrated in connection with a 2700 gallon central system and aluminum can drawing facility. The abnormal condition which occurred was the undetected rupturing of a pipe in a water cooling line which occurred about midway through the time period depicted by the charts of FIGS. 7 and 8. The jagged characteristic on the conductivity chart of FIG. 7 reflects the automatic fluid makeup which causes the introduction of clean fluid from the water supply line 63 and the concentrate tank 65 into the central system 30. This fluid addition generally causes a decline in conductivity as the other components of the fluid which tend to increase the conductivity are diluted.

The data shown on the charts of FIGS. 7 and 8 follow a period during which the system experienced considerable difficulty in maintaining a proper mix ratio and pH stability. An unidentified leak was apparently the cause which was manifested by the measurements taken during the period shown in the graphs of FIGS. 7 and 8 when the leakage problem becomes worse. This more serious leakage problem is coincident with the significant drop in conductivity shown in FIG. 7 from approximately 3,000 micromhos to approximately 2,600 micromhos during a period of approximately 24 hours. The drop in conductivity was caused by the replacement of the leakage fluid with makeup fluid of lower conductivity which maintained the fluid level in the reservoir 31 approximately constant. In the system depicted here, the leak was repaired and the conductivity then rose as shown in FIG. 7 as the fluid component concentrations were reestablished by the addition of additives.

As FIG. 8 illustrates, however, the undetected leak prior to the measured period resulted in bacteria growth which was due to loss of bacteriacides in the fluid. This was brought back to a normal level by the addition of additives which then cause the dissolved oxygen to be maintained for a period as shown in FIG. 8. Specifically, with the increase leakage which corresponds to the declining conductivity of FIG. 7, the fluid again became very lean and the growth of microorganisms gradually increased following the dilution of the fluid. This microbiological growth caused a decrease in the dissolved oxygen which was reflected by the decrease shown in FIG. 8. After the leakage problem was corrected, the addition of bacteriacides restored the dissolved oxygen and checked the bacterial growth.

Referring to FIGS. 9 and 10, the dissolved oxygen and pH of a central system 30 of approximately 17,000 gallons utilizing a semi-synthetic metalworking fluid for machining operations upon aluminum housings is illustrated. The central system 30 in question had severe mold growth. In the plots illustrated in FIGS. 9 and 10, the facility had a routine practice of adding microbiocide at double strength on Fridays and on Sunday mornings before shutting down for the weekend and restarting the system for the next week. The severe mold growth of the system did not show up on culture counts performed by the facility but the mold could be visually seen in the tank 31 and return flume 46 and removed mechanically.

Referring to FIG. 9, the extremely low dissolved oxygen content plotted is characteristic of the condition inducive to mold growth. The vertical rises in dissolved oxygen coincide with the addition of biocide. The effect of these additions, however, as shown in FIG. 9 was significant but temporary. In the pH chart of FIG. 10 it is seen that the pH began to increase with the addition of microbiocide but that this impact too was shortlived. The condition illustrated in FIGS. 9 and 10 was such that a replacement of the fluid and a cleaning of the system was required in that the mold growth of the system had gone beyond the point of controllability by chemical means.

According to the embodiment of the invention illustrated, data of the type described above can be manually analyzed or, through the provision of appropriate algorithms, automatically analyzed. The algorithms may be simple stored tables which contain data or curves of information acquired from previous measurements or experience with the specific system being controlled, or similar systems, correlating parameter variations with corrective actions which have proved effective. Preferably, a combination of both automated and manual analysis and decision making is employed to control the central systems 30 of the plants monitored in accordance with the system depicted in FIG. 1 to control the fluids in accordance with commands instituted in response to the analyzed data. In response to such analysis, control signals are initiated either through the remote communication system 13 from the central location 11 to the plants 12, 12a, 12b or by other methods intended to communicate the action needed to correct the system deviations detected by the monitoring process. This control information may be input to the controller 72 either through the computer 75 in response to information received through the modem 92 or through a panel on the controller 72 by the manual acts of the operator 79 then in response to data provided to him on the monitor 77 or printer 78. The information is provided either in the form of data from the computer 75 or in the form of commands or recommendations from the central monitoring center 20 at the location 11.

Having described the invention, what is claimed is the following:

1. A method of maintaining the condition of an aqueous metalworking fluid at a metal working location having located thereat a plurality of metalworking machines, a central reservoir containing a volume of the aqueous metalworking fluid sufficient to service the plurality of machines, and means connected to the machines and the reservoir for circulating fluid through the machines and the reservoir, the fluid being made up of components that include a lubricant and water and being used under conditions that will support contaminating biological activity within it, the method comprising the steps of:
   monitoring, in-line with the fluid circulating means, a plurality of different components of the fluid and producing in real time for each monitored component a measurement signal responsive thereto, including an oxygen measurement signal responsive to the dissolved oxygen content of the fluid and a pH measurement signal responsive to the hydrogen ion content of the fluid;
   generating, in response to the oxygen measurement signal and the pH measurement signal, at least one monitoring signal carrying information of the pH and oxygen content of the fluid;
   analyzing the pH and oxygen content information carried by the monitoring signal; and
   modifying, in real time, the content of a third component of the monitored fluid in response to the analysis to control the biological activity therein.

2. The method of claim 1 wherein:
   the monitoring step includes the steps of monitoring the dissolved oxygen and pH for time varying changes in the content thereof in the fluid; and
   the analyzing step includes the step of analyzing information derived from the measurement signals for time varying changes in the content of the monitored components in the fluid.

3. The method of claim 1 wherein:
   the modifying step includes the step of adding the third component to the fluid different from the monitored dissolved oxygen and pH parameters to control biological activity within the monitored fluid in response to the analysis.

4. The method of claim 1 wherein:
   the third component content modifying step includes the addition of a biocidal agent to directly affect biologically active components in the fluid.

5. The method of claim 1 further comprising the steps of:
   establishing a communication link between the metal working location and a remote monitoring facility;
   transmitting the monitoring signal through the communication link to the remote monitoring facility;
   the analyzing step including the step of analyzing at the remote location the information carried by the monitoring signal and deriving therefrom information relating to the biological activity of the fluid; and
   comparing the derived information with predetermined criteria and generating in response to a result of the comparison an output signal carrying information relating to the maintenance of the composition of the fluid to control biological activity therein.

6. The method of claim 5 for monitoring aqueous metalworking fluid at plurality of metal working locations for biological activity, the method comprising the steps of:
   sensing at each metal working location, in real time and in-line with the circulating fluid, at least two components of the metalworking fluid that have a tendency to vary in response to the biological activity within the fluid;
   producing at each metal working location at least one monitoring signal carrying data responsive to the content of the sensed component in the fluid thereat;
   selectively establishing the communications link between a selected one of the metal working locations and the central monitoring facility located remote from the metalworking locations;
   transmitting data from the selected metalworking location to the central monitoring facility over the communications link; and
   communicating to the selected metalworking location, in response to the determination, information relating to the addition of the third component to the fluid at the selected metalworking location to control the biological activity in the fluid; and
   the modifying step includes the step of adding a quantity of the third component to the fluid in response to the information communicated from the central monitoring facility.

7. The method of claim 1 further comprising the steps of:
   monitoring, in-line with the fluid circulating means, a plurality of different parameters of the fluid and producing in real time for each parameter a measurement signal responsive thereto, including, in addition to the first component and second component measurement signals, a fluid temperature measurement signal responsive to the temperature of the fluid and a conductivity measurement signal responsive to the electrical conductivity of the fluid;
   generating, in response to the temperature measurement signal and the conductivity signal, at least one monitoring signal carrying information of the temperature and conductivity of the fluid;
   analyzing the temperature and conductivity information carried by the monitoring signal; and
   initiating, in real time, action to control the concentration and pH of the fluid in response to the analysis.

8. A method of controlling the biological contamination of an aqueous metalworking fluid at a metal working location having located thereat a plurality of metalworking machines, a central reservoir containing a volume of the aqueous metalworking fluid sufficient to service the plurality of machines, and means connected to the machines and the reservoir for circulating fluid through the machines and the reservoir, the fluid being made up of components that include a lubricant and water and being used under conditions that will support contaminating biological activity within it, the method comprising the steps of:
   monitoring the fluid in real time by sensing in-line with the circulating fluid at least two of a plurality of different parameters of the fluid, which have a tendency to vary differently in response to biological activity within the fluid;

producing, in real time, measurement signals responsive to each monitored parameter;

analyzing, in real time, information derived from the measurement signals for time varying changes in the sensed parameters caused by biological activity within the fluid; and modifying the fluid, in real time, to reduce the biological activity within the fluid in response to the analysis.

9. The method of claim 8 wherein:

the monitored parameters that vary in response to biological activity include pH and dissolved oxygen; and the fluid modifying step includes the step of adding a biocidal agent to the fluid to directly reduce biological activity in the fluid.

10. The method of claim 8 wherein:

the modifying step includes the step of initiating action to modify a third parameter of the fluid different from the at least two monitored parameters to control biological activity within the monitored fluid in response to the analysis and to thereby prevent further variation in the monitored parameters caused by the biological activity.

11. The method of claim 10 wherein:

the action to modify the third parameter includes the addition of a biocidal agent to directly affect biologically active components in the fluid.

12. The method of claim 8 further comprising the steps of:

establishing a communication link between the metal working location and a remote monitoring facility;

transmitting the monitoring signal through the communication link to the remote monitoring facility;

the analyzing step including the step of analyzing at the remote location the information carried by the monitoring signal and deriving therefrom information relating to the biological activity of the fluid; and comparing the derived information with predetermined criteria and generating in response to a result of the comparison an output signal carrying information relating maintenance of the composition of the fluid to control biological activity therein.

13. The method of claim 12 for monitoring aqueous metalworking fluid at plurality of metal working locations for biological activity, the method comprising the steps of:

sensing at each metal working location, in real time and in-line with the circulating fluid, at least two parameters of the metalworking fluid that have a tendency to vary in response to the biological activity within the fluid;

producing at each metal working location at least one monitoring signal carrying data responsive to variations in the sensed parameters;

selectively establishing the communications link between a selected one of the metal working locations and the central monitoring facility located remote from the metalworking locations;

transmitting data from the selected metalworking location to the central monitoring facility over the communications link; and communicating to the selected metalworking location, in response to the determination, information relating to biological activity in the fluid at the selected metalworking location that may require corrective action.

14. The method of claim 8 further comprising the steps of:

monitoring, in-line with the fluid circulating means, a plurality of different parameters of the fluid and producing in real time for each parameter a measurement signal responsive thereto, including, in addition to the first and second measurement signals, an fluid temperature measurement signal responsive to the temperature of the fluid and conductivity signal responsive to the electrical conductivity of the fluid;

generating, in response to the temperature measurement signal and the conductivity signal, at least one monitoring signal carrying information of the temperature and conductivity of the fluid;

analyzing the temperature and conductivity information carried by the monitoring signal; and initiating, in real time, action to control the concentration and pH of the fluid in response to the analysis.

15. A method of controlling the biological activity in an aqueous metalworking fluid at a metal working location having located thereat a plurality of metalworking machines, a central reservoir containing a volume of the aqueous metalworking fluid sufficient to service the plurality of machines, and means connected to the machines and the reservoir for circulating fluid through the machines and the reservoir, the method comprising the steps of:

sensing, in real time and in-line with the circulating fluid at the metal working location, the amount of oxygen dissolved in the fluid;

producing, in real time, a monitoring signal carrying information responsive to the amount of dissolved oxygen sensed;

establishing a communication link between the metal working location and a remote monitoring facility;

transmitting the monitoring signal through the communication link to the remote monitoring facility;

analyzing at the remote location the information carried by the monitoring signal and deriving therefrom information relating to the biological activity of the fluid;

comparing the derived information with predetermined criteria and generating in response to a result of the comparison an output signal carrying information relating maintenance of the composition of the fluid to control biological activity therein;

transmitting the output signal from the remote facility to the metalworking location; and modifying the composition of the monitored fluid in response to the output signal to reduce the biological activity therein.

16. The method of claim 15 wherein the transmission step is performed over a telephone communication link between the remote location and the system.

17. The method of claim 15 further comprising the step of initiating the transmission in response to an interrogation signal from the remote facility.

18. The method of claim 15 further comprising the step of initiating the transmission in accordance with a predetermined schedule.

19. The method of claim 15 further comprising the step of initiating from the site of central system the transmission in response to information derived in the monitoring step.

20. The method of claim 15 further comprising the steps of:

storing data derived in the monitoring step and subsequently generating the signal from the stored data representative of the history of the monitored parameter of the fluid.

21. The method of claim 15 wherein the transmission step is initiated at programmed intervals to transmit the plurality of signals for analysis to the remote location, and is initiated at more frequent intervals to test the information for specific characteristics.

22. A method of controlling the biological activity in aqueous metalworking fluids at each of a plurality of different metal working locations, wherein each metal working location has located thereat a plurality of metalworking machines, a central reservoir containing a volume of the aqueous metalworking fluid sufficient to service the plurality of machines at the location, and means connected to the machines and the reservoir for circulating fluid through the machines at the location and the reservoir, the method comprising the steps of:

sensing at each metal working location, in real time and in-line with the circulating fluid, at least two parameters of the metalworking fluid that have a tendency to vary in response to the activity within the fluid at the respective location;

producing at each metal working location a monitoring signal carrying data responsive to variations in the sensed parameter;

selectively establishing a communications link between a selected one of the metal working locations and a central monitoring facility located remote from the metalworking locations, the facility having means thereat for analyzing data received from the locations and for generating output signals containing information for the control of the compositions of metalworking fluids in response to the analyses;

transmitting data from the selected metalworking location to the central monitoring facility over the communications link;

analyzing the transmitted data at the monitoring facility to determine whether corrective action is needed at the selected metalworking location to control biological activity in the fluid thereat, and producing an output signal in response to a determination that corrective action is needed;

communicating from the monitoring facility to the selected metalworking location, in response to the determination, the output signal carrying information relating to corrective action to be taken; and initiating corrective action to control biological activity in the fluid at the selected metalworking location in response to the output signal communicated from the monitoring facility.

23. The method of claim 22 wherein:

the output signal transmitting and communicating steps include the step of transmitting a control signal from the remote facility to the selected metalworking location in response to the determination and automatically controlling equipment at the metalworking location in response thereto to perform the needed corrective action on the fluid thereat to control the biological activity therein.

24. The method of claim 22 wherein the communicating step further comprises the step of:

communicating to an operator at the fluid site information in response to the signal from the remote location.

25. The method of claim 24 further comprising the step of:

modifying the fluid at the fluid site in response to the information communicated to the operator.

26. The method of claim 22 further comprising the step of:

controlling in real-time the condition of the fluid in response to the information communicated from the remote facility.

27. The method of claim 26 further comprising the step of:

adding a fluid component to the fluid in response to the signal from the remote location.

28. The method of claim 27 further comprising the step of:

controlling a flow control device connected with the central system and a supply of the fluid component to add the component to the monitored fluid.

29. A system for maintaining the condition of an aqueous metalworking fluid at a metal working location having located thereat a plurality of metalworking machines, a central reservoir containing a volume of the aqueous metalworking fluid sufficient to service the plurality of machines, and means connected to the machines and the reservoir for circulating fluid through the machines and the reservoir, the fluid being made up of components that include a lubricant and water and being used under conditions that will support contaminating biological activity within it, the system comprising:

an oxygen sensor in contact with the circulating fluid operable to generate an oxygen measurement signal responsive to the dissolved oxygen content of the fluid;

a pH sensor in contact with the circulating fluid for generating a pH measurement signal responsive to the hydrogen ion content of the fluid;

a programmed digital computer responsive to the measurement signals and programmed to analyze pH and oxygen content information carried by the measurement signals and to generate an output signal in real time carrying information indicating action to control biological activity within the fluid in response to the analysis; and means connected in the system and responsive to the output signal for carrying out the indicated action by controlling a parameter of the fluid, different from the sensed pH and oxygen, to control biological activity within the fluid.

30. The system of claim 29 wherein:

the controlling means includes biocidal agent supply means connected to the reservoir or circulating means for adding a biocidal agent to the fluid in response to the output signal.

31. A system for controlling the biological contamination of an aqueous metalworking fluid at a metal working location having located thereat a plurality of metalworking machines, a central reservoir containing a volume of the aqueous metalworking fluid sufficient to service the plurality of machines, and means connected to the machines and the reservoir for circulating fluid through the machines and the reservoir, the fluid being made up of components that include a lubricant and water and being used under conditions that will support contaminating biological activity within it, the system comprising:

means connected in-line with the recirculating fluid for monitoring in real time at least two components of the fluid which have a tendency to vary differently in response to biological activity within the fluid and for producing, in real time, measurement signals responsive to the monitored components;

a programmed computer including means responsive to the measurement signals for analyzing, in real time, information derived from the measurement signals for time varying changes in the monitored components, and for generating in response to the analysis an output signal carrying information representative of the biological activity within the fluid and indicative of the addition of a third component, different from the monitored components, that is effective to directly control the biological activity within the fluid; and means connected to the system for automatically adding the third component to the fluid in response to the output signal to control the biological activity of the fluid.

32. The system of claim 31 wherein:

the third component is a biocidal agent; and the third component adding means includes a supply of biocidal agent and means connected to the reservoir or circulating means for adding a biocidal agent from the supply to the fluid in response to the output signal.

33. A system for monitoring and controlling microbiological activity in an aqueous metalworking fluid at a metalworking location having located thereat a plurality of metalworking machines, a central reservoir containing a volume of the aqueous metalworking fluid sufficient to service the plurality of machines, and means connected to the machines and the reservoir for circulating fluid through the machines and the reservoir, the system comprising:

means connected in-line with the circulating fluid at the metal working location for sensing at least two parameters of the fluid thereat including the amount of oxygen dissolved in the fluid;

means connected to the sensing means for producing, in real time, a monitoring signal carrying information responsive to the sensed parameters including amount of dissolved oxygen sensed;

a monitoring facility remote from the metalworking location having located thereat programmed computer means for analyzing information carried by a monitoring signal communicated thereto and for deriving therefrom information relating to the biological activity of a monitored fluid;

a communication link connected between the metal working location and the remote monitoring facility;

means at the metalworking location for transmitting the monitoring signal through the communication link to the remote monitoring facility;

the computer means at the monitoring facility being programmed to generate, in response to the information relating to the biological activity within the fluid, an output signal carrying information relating maintenance of the fluid at the metalworking location to control biological activity therein and means at the monitoring facility for transmitting the output signal to the metalworking location over the communication link.

34. The system of claim 33 further comprising:

means at the metalworking location for automatically modifying the composition of the monitored fluid in response to the information carried by the output signal.

35. The system of claim 34 wherein the fluid composition modifying means comprises a fluid component source connected to the central system and a fluid flow control device operable in response to the information carried by the output signal to control the introduction of the component from the source into the fluid.

36. The system of claim 33 wherein:

the computer means at the monitoring facility includes means for comparing the monitor signals with stored fluid condition criteria and for generating a predetermined response to an anticipated result of the comparison; and the transmitting means at the monitoring facility includes means for generating the output signal carrying information for controlling the composition of the fluid in accordance with the predetermined response.

37. A system for monitoring the condition of an aqueous metalworking fluid at plurality of metal working locations for biological activity and for providing information to the locations for the maintenance of the fluid thereat, wherein each metal working location has located thereat a plurality of metalworking machines, a central reservoir containing a volume of the aqueous metalworking fluid sufficient to service the plurality of machines at the location, and means connected to the machines and the reservoir for circulating fluid through the machines at the location and the reservoir, the system comprising:

means at each metalworking location, for sensing in real time and in-line with the circulating fluid, at least two parameters of the metalworking fluid that have a tendency to vary in response to the biological activity within the fluid;

means at each metalworking location for generating a monitoring signal carrying data responsive to variations in the sensed parameters;

a monitoring facility located remote from the metalworking locations and having programmed computer means thereat for analyzing data received from the locations and for generating output signals containing information for the control of the compositions of metalworking fluids in response to the analyses;

means for selectively establishing telephone communications links between each metalworking location and the monitoring facility;

means at each of the metalworking locations for transmitting data from the selected metalworking location to the central monitoring facility over the established communications link; and means at the monitoring facility for receiving over an established communications link the transmitted data from the selected metalworking location for transmitting over an established communications link the output signal to the selected location containing information for the control of the biological activity of metalworking fluid thereat.

* * * * *